United States Patent [19]

Moore

[11] Plant 4,867

[45] Jul. 20, 1982

[54] ROSE PLANT

[76] Inventor: Ralph S. Moore, 2519 E. Noble Ave., Visalia, Calif. 93277

[21] Appl. No.: 212,016

[22] Filed: Dec. 1, 1980

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by its variegated (striped) buds and flowers of red and white.

1 Drawing Figure

The present invention relates to a new and distinct variety of hardy, dwarf, bush type rose plant of the miniature class; the variety being primarily characterized — as to novelty — by the red and white striped flowers which generally open quite flat and hold colors extremely well.

The variety is further characterized by:

An abundance of bloom, with flowers usually borne singly, but also several to the stem in small cluster.

Little or no fragrance.

A plant which is moderately vigorous, of rounded, upright shape with small semi-glossy to matt foliage with pointed leaflets; the buds being similar in form to Yellow Doll (miniature — U.S. Plant Pat. No. 2,450) and flowers being similar in form to Judy Fischer (miniature — U.S. Plant Pat. No. 3,137).

The plant, which has a normal height of 8–10 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired — florabunda) as the seed parent and an unnamed seedling (miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety identification: MORtrip (commercial synonym: Crazy Quilt).

Flowers borne: Singly and several together (3 to 5) on slender wiry stems.

Quantity of bloom: Moderately abundant both outside and in greenhouse.

Bud:

*Peduncle.*—Medium to short length; slender but sturdy; erect; medium green, sometimes tinted bronze (outdoors); with no prickles and numerous very short fuzz-like hairs.

*Before calyx breaks.*—Size — small. Form long, ovoid to pointed, with several small foliaceous appendages on surface of bud; with foliaceous parts extending beyond the tip of the bud equal to one-half or more of its length.

*Color.*—Medium green, occasionally tinted with bronze (outdoors).

*As calyx breaks.*—Color — white or red (or both).

*Opening.*—Opens well in all weather.

Bloom:

*Size when fully open.*—Small, averaging about 30 – 35 mm ($1\frac{1}{4}''$).

*Petalage.*—Double — averaging about 40 (or more) petals, arranged regularly plus several small petaloids.

*Form.*—Cupped at first becoming quite flat with petals rolled slightly outward and downward. Open flowers usually have no stamens.

Petals: Fairly thick; satiny on inside and on outside surface.

*Shape.*—Outside petals, broad lanceolate with nearly round tip or very short acute tip; intermediate — broad lanceolate with nearly round or short acute tip; inside — lanceolate with acute tip.

Color: Newly opened flower from a plant grown in plastic greenhouse (November 1980), Visalia, Calif.:

*Outside petal.*—Outside surface — white or near white and striped with red of a shade near Rose Red 724 but overlaid or veined with darker red (near Cardinal Red 822 or 822/1) to give a darker red effect; becoming white or greenish yellow at base. Inside surface — similar color to outside surface — the red areas being near Rose Red 724 with the shading or veining similar to or even darker than on reverse side.

*Intermediate petal.*—Outside surface similar to outside petal. Inside surface similar to outside petal.

*Inner petal.*—Outside surface — similar to intermediate petal; inside surface — similar to intermediate petal.

*General color effect.*—Buds and newly opened flowers — red and white stripes (or variegation) with no two petals alike. Three days open — color — similar to fresh open flowers, but less bright. Behavior — opens well in all weather.

Spent petals or flowers drop off. Flower longevity (July - August 1980) — plant in pot 6-10 days or longer. Cut flowers at living room temperature 5-7 days or longer.

Reproductive organs:

*Stamens.*—Few — usually none.
*Filaments.*—Varying length (if present).
*Anthers.*—Yellow (if present).
*Pollen.*—None.
*Pistils.*—Average number.
*Styles.*—Varying length; near white; bunched.
*Ovaries.*—All enclosed in calyx.
*Hips.*—None.
*Sepals.*—Permanent; spear shaped; recurved.
*Seed.*—None.

Foliage:

*Leaves.*—Compound of five (sometimes three or seven) leaflets; medium small; leathery; semi-glossy to matt.
*Leaflets.*—Shape: broad, lanceolate; apex acute; base — acute — sometimes rounded.
*Color.*—Medium green; new growth — normal (medium) green (sometimes tinted reddish).
*Rachis.*—Medium strength; upper side may have a few short hairs, grooved; underside may have several small thorns (or claws) and few to several tiny short prickles.
*Stipules.*—Medium to short length; medium width; medium to short length narrow points which turn out usually at about 45 degrees or more.

Growth:

*Habit.*—Dwarf; bushy; rounded; much branched.
*Growth.*—Moderately vigorous; internodes short.
*Canes.*—Medium; slender; sturdy.
*Main stems.*—Color: medium green.
*Thorns.*—Several — of varying size and length. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers variegated or striped, in differing degrees and patterns, with red and white, the bud being pointed in the early opening stage, resembling in form Yellow Doll (miniature — U.S. Plant Pat. No. 2,450), with the full open flower being rather flat with many (40 or more) petals ranging from long (outer petals) to quite short (inner petals); and further characterized by a plant of compact, vigorous, well rounded shape, with main stems and shoots of average thorniness, the said plant being easy to propagate from soft wood cuttings, with an abundance of small semi-glossy to matt foliage, the flowers being born singly or several to the stem in clusters.

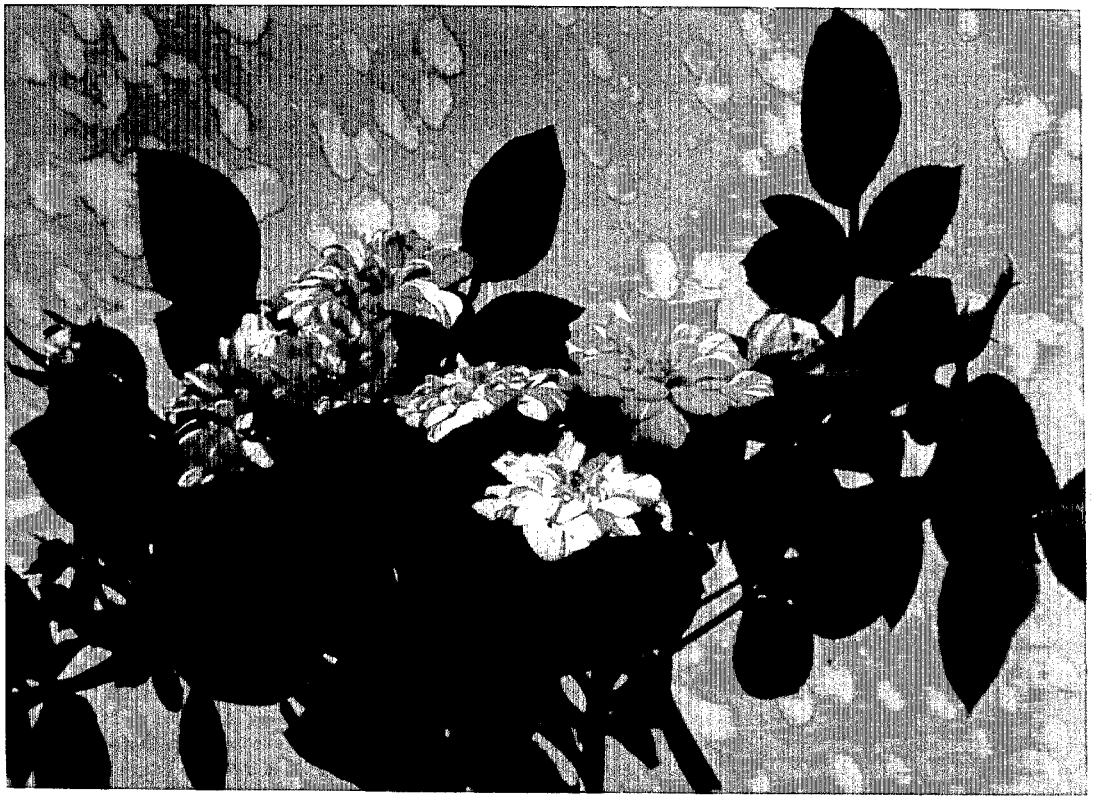

* * * * *